United States Patent
Markart

[19]

[11] Patent Number: 6,027,689
[45] Date of Patent: Feb. 22, 2000

[54] TEST CARD FOR AN OPTICAL OR ELECTRICAL DETERMINATION OF THE CONCENTRATION OF A SUBSTANCE IN A LIQUID

[75] Inventor: Ernst Markart, Munich, Germany

[73] Assignee: LRE Technology Partner GmbH, Munich, Germany

[21] Appl. No.: 09/145,071

[22] Filed: Sep. 1, 1998

[30] Foreign Application Priority Data

Feb. 13, 1998 [DE] Germany ................. 198 06 054

[51] Int. Cl.[7] .................................................. G01N 33/48
[52] U.S. Cl. .............................. 422/58; 422/61; 422/56
[58] Field of Search ............................... 422/56, 58, 61, 422/99, 102, 104

[56] References Cited

U.S. PATENT DOCUMENTS

| | | | |
|---|---|---|---|
| 3,915,639 | 10/1975 | Friedenberg | 422/56 |
| 5,017,342 | 5/1991 | Haberzettl et al. | 422/102 |
| 5,183,742 | 2/1993 | Omoto et al. | 422/58 |
| 5,597,532 | 1/1997 | Connolly | 422/58 |
| 5,635,403 | 6/1997 | Bailey | 422/58 |

*Primary Examiner*—Lyle A. Alexander
*Attorney, Agent, or Firm*—McCormick, Paulding & Huber LLP

[57] ABSTRACT

A test card for use with a measuring device for evaluating the concentration of a substance in a liquid, such as a substance in a body liquid, is made up of a number of layers of material preferably capable of being united with one another in a continuous process as the layers are unrolled from associated supply rolls. Each test card includes a plurality of individually usable test sections connected with one another and arranged in succession along the longitudinal direction of the card. The layers of material making up the card include at least a reaction layer and an overlying cover layer with the cover layer having a drop application opening in each test section for receiving a drop of the liquid to be accommodated. A distribution layer and a carrier layer of material may also be included in the card with the carrier layer in each test section having a measuring opening registering with the drop application opening, and lines of weakening are provided between neighboring test sections to allow easy removal of a used test section from the remaining ones.

37 Claims, 2 Drawing Sheets

TEST CARD FOR AN OPTICAL OR ELECTRICAL DETERMINATION OF THE CONCENTRATION OF A SUBSTANCE IN A LIQUID

FIELD OF THE INVENTION

The invention concerns a test card for an optical or electrical determination of the concentration of a substance in a fluid, especially a body fluid, the card having a plurality of test sections connected to one another, and arranged in succession to one another in the longitudinal direction of the strip shaped card. One such test card is described in old German patent application 19 714 674. In that application, the card consists of several test strips arranged in a common sleeve. The card is inserted with the sleeve in a test device. To make a measurement, the card is pulled out of the sleeve by the width of a strip, so that the test field is exposed for the dropping on of the fluid and for the carrying out of the measurement. After such measurement, the used test strip can be separated from the remainder of the card.

BACKGROUND OF THE INVENTION

The invention has, as its object, to simplify the production of such a test card.

SUMMARY OF THE INVENTION

This object is solved in accordance with the invention in that the test card has a reaction layer and a cover layer, with the cover layer for each test section having formed therein a drop application opening for the dropping on of the liquid to be investigated.

The test card of the invention can be so manufactured that the different layers or plies run together from supply rolls and are then joined with one another. For forming the card, the layers so joined with one another need only be separated from one another at regular spacings.

In a preferred embodiment of the invention, the reaction layer is enclosed between the cover layer and a carrier layer. In use, this diminishes the danger of the unused test sections of a card coming into contact with the air through a device sided seal as soon as the first test section is used, which has been the case in previous solutions.

To accelerate the distribution of the liquid in the reaction layer and to make such distribution uniform, a distribution layer can be provided between the reaction layer and the cover layer.

The cover layer can be made from an absorbent material so that liquid running from the edge of the drop application opening can be absorbed by the covering material and thereby avoid smearing of the measuring device in which the test card is inserted. With respect to hygiene, it can also be practical that the cover layer be made from a hydrophobic material so that the liquid exhibits no tendency to run from the edge of the drop application opening over the cover layer.

The carrier layer can have a measuring opening for each test section, which measuring opening is in the form of an elongated hole having a longitudinal axis running in the direction of the longitudinal axis of the strip in order to have a certain tolerance in the positioning of each test section in the measuring device. Also it is practical if the dimensions of the drop application opening in the cover layer are smaller than the measurements of the measuring opening in the carrier layer.

In an optical measurement, depending on circumstances, a measuring opening can be eliminated, if the carrier layer is made from a transparent material through which an optical measurement can be made.

The carrier layer and the cover layer advantageously run continuously in the longitudinal direction of the strip, whereas the reaction layer in which the test reactions with the liquid to be investigated take place, and the distribution layer, which serves to provide a uniform distribution of the applied liquid over the reaction layer, are separated between each two neighboring test sections in order to hinder the flow of the liquid from the immediately used test section to a neighboring test section.

The separation can result from a gap passing through the involved layers, which gap, for example, is semi-circularly curved around the drop application opening. The gap can pass in registration through all of the layers with the smaller reaction layer and distribution layer being completely separated while the carrier layer and the cover layer are only partially separated and connected together at their edge areas. This simplifies the manufacturing, since the separation gaps can be created by means of a stamping machine after the joining of the different layers or plies.

Practically, the reaction layer has a larger surface in comparison to the distribution layer and is, therefore, with reference to the longitudinal direction of the strip wider than the distribution layer in order to avoid the distribution layer leaking fluid outwardly from the reaction layer.

To retain the reaction capability of the reaction until the time of use of the involved test section and to avoid an influence from the ambient air and moisture as far as possible, it is practical to arrange a drying medium next to the reaction layer, which drying medium absorbs the moisture of the surrounding air. One can, however, also pre-dry the cover layer and/or the carrier layer so that they, in the manufacturing process absorb possibly enclosed air moisture and inhibit a premature reaction in the reaction layer with the moisture of the surrounding air.

To make possible a mechanical transport of the test cards in a measuring device, the test cards can have recesses in their longitudinal edges for the test card transport. Practically, these recesses are provided between each two neighboring test sections so that, as the case may be, they also simplify the separation of the individual test sections from one another. In connection with this, registered lines of weakening can be provided in the layers between each two neighboring test sections.

To simplify the insertion and manual transportation of the test card in the measuring device, one longitudinal end of the test card can be formed as a gripping end. Practically, this gripping end is formed larger than the remainder of the test card so that, at the same time, an incorrect insertion of the test card into the measuring device is hindered.

To further simplify the insertion of the test card into the measuring device, the test card can have inclined insertion guide edges at its end opposite to the gripping end.

To assure that no liquid escapes from the immediately used test section to the not yet used neighboring test section, each test section can have a seal ring surrounding the drop application opening and/or the measuring opening, which is intended for cooperation with a corresponding sealing surface of the measuring device. The sealing ring can, at the same time, consist of a suitable drying medium and thereby take on the drying function.

The test strips for the carrying out of the previously mentioned investigations must in general have accompanying information which includes manufacturing data and data characteristic for the concerned reaction. Practically, this information is provided on the test card so that by mistake an incorrect test card cannot be inserted and the device with assurance will contain the required data for the evaluation of the test. The information can be in the form of a bar code printed onto the test card, so that it can be read upon insertion of the test card into the test device. However, as the information carrier, a magnetic strip applied to the test card can also be used. Another possibility exists in the information carrier being a hologram which is either applied to or embossed into the test card. Another possibility is to provide a resistance layer on the test card and to use the resistance value of this layer as a key for calling up the specified test program. Should extensive information have to be supplied, a memory chip can also be provided on the test card. Further, it is also possible to provide a test card identification in the form of a perforation code in the card.

In the case of test cards whose test fields are to be measured by way of electrical currents, it is proposed in accordance with the invention that, on the surface of the cover sheet facing the reaction layer and/or the face of the carrier layer facing the reaction layer and within each test section, two electrical contact paths be provided which stand in connection with one another through a section of the reaction layer serving as the test field. To permit a continuous manufacture of the test cards, it is practical if at least one of the contact paths is continuous in the longitudinal direction of the cards. If two contact paths are to be continuous in the longitudinal direction of the cards, they must be interrupted between the test sections.

In a preferred embodiment, the contact paths are interrupted by the transport recesses, so that a separate interruption of the contact paths is not necessary.

In another preferred embodiment of the invention, the contact paths, at least in the area of each test field, can project laterally from the cover layer. Thereby the contact paths can also be used as position indicators for the position of the test sections. When the measuring electrodes comes into contact with the contact paths, the electrical resistance between the measuring electrodes is changed. This signal can, therefore, be used as an indication that the test section has taken on the correct position for the carrying out of the measurement.

To reduce the cost of the relatively expensive reaction material, the reaction layer can consist of a chain of test fields which are connected with one another by thin bridges. In this way there remains on one hand the advantage of continuous material feed, and on the other hand, only so much material for the reaction layer is used as is absolutely necessary.

Further features and advantages of the invention will be apparent from the following description, which in connection with the accompanying drawings explains the invention by way of exemplary embodiment.

DETAILED DESCRIPTION OF THE PREFERRED EMBODIMENTS

Figure 1:
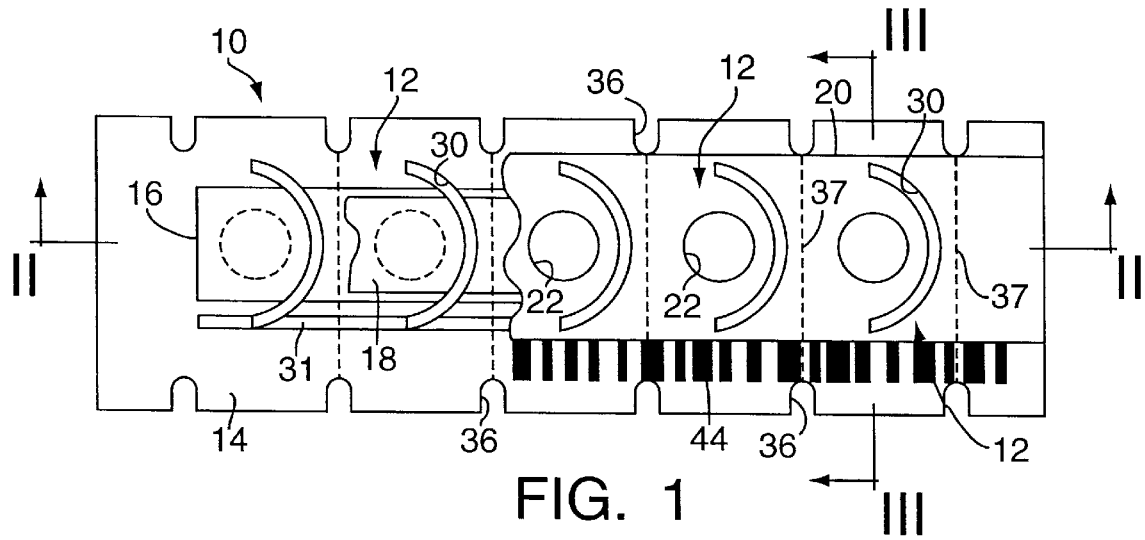
FIG. 1—A schematic plan view of a test card in accordance with the invention and with five test sections, FIG. 2—A section through the test card of FIG. 1 taken along the line II—II of FIG. 1, FIG. 3—A section through the test card of FIG. 1 taken along the line III—III of FIG. 1, FIG. 4—A partial section corresponding to FIG. 3 through a modified embodiment of the test card, FIG. 5—A schematic plan view of a test card comprising a further embodiment of the invention, FIG. 6—A schematic cross-section through a test card with only two layers, FIG. 7—A schematic cross-section through a test card with three layers, FIG. 8—A schematic plan view of the carrier layer of a test card with test fields and printed contact paths, FIG. 9—A plan view corresponding to FIG. 8 with a continuous contact path, FIG. 10—A plan view corresponding to one of FIG. 8 or 9 with two continuous contact paths, FIG. 11—A view corresponding to FIG. 10 for a modified embodiment of the test card, FIG. 12—A view corresponding to FIG. 8 of a further embodiment of the test card, and FIG. 13—A schematic plan view of a cover layer for a test card with a special formed reaction layer.
Figure 2:
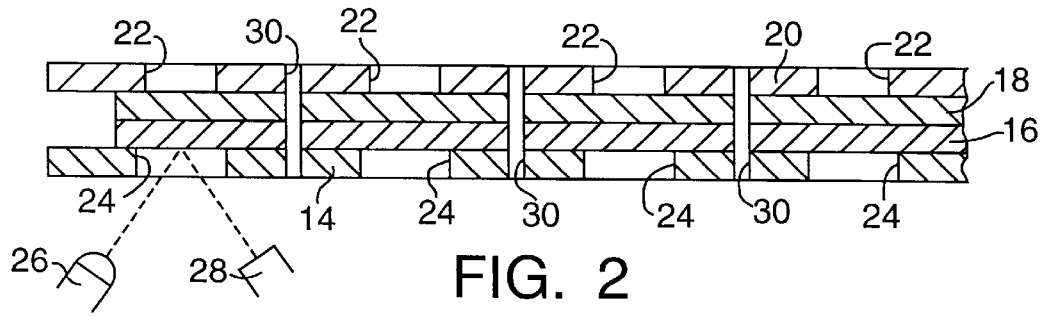

FIGS. 1 and 2 show a test card, indicated generally at 10, in the form of an elongated strip with five test sections 12 arranged following one another in the longitudinal direction of the strip.

The test card consists of a carrier layer or support 14, on which are arranged in overlying relationship to one another a reaction layer 16, a distribution layer 18 and a cover layer 20. A circular-shaped drop application opening 22 is formed in the cover layer in the middle of each test section 12. Concentric therewith the carrier layer 14 has a measuring opening 24, the diameter of which is equal to or somewhat larger than the diameter of the drop application opening 22, as can be seen in FIG. 2.

If a liquid to be investigated is applied to the distribution layer 18 of the involved test section 12 through the drop application opening 22, the distribution layer 18 distributes the liquid uniformly over the reaction layer lying under the distribution layer. In the reaction layer, there results a reaction of certain chemicals with the substance whose concentration in the applied liquid is to be determined. This reaction leads to a color change which can be measured with the help of an optical measuring device including a light source 26 and a receiver 28.

To inhibit a carrying over of liquid from the immediately used test section to a following not yet used test section 12, the reaction layer 16 and the distribution layer 18 of the individual test sections 12 are separated from one another by a curved gap or slot 30, for example of semi-circular shape, about the drop application opening 22. In the illustrated exemplary embodiment, this gap 30 also passes through the cover layer 20 and the carrier layer 14. As can be seen in FIG. 1, this gap 30 indeed separates entirely the narrower inwardly lying layers 16 and 18, but not however the outer layers 14 and 20 which remain connected with one another along their longitudinal edges. This solution has a technical manufacturing advantage, since the separating gap 30 after the joining of the, for example, four layers can be created by stamping. If on the other hand the separating gap 30 is to separate the individual test sections 12 from one another only in the region of the inner layer 16 and 18, then the separating cut must be carried out before the application of the cover layer 20. This is possible to do but is more expensive as to production technique.

In FIG. 1 one sees further that the reaction layer 16 is somewhat broader than the distribution layer. This assures that no liquid escapes over the edge of the reaction layer 16 where it possibly cannot be absorbed. Next to the reaction layer, as shown in FIG. 1, is further a strip 31 of a drying medium.

Figure 3:
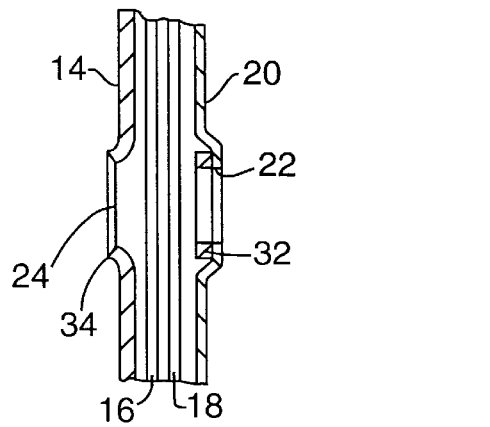
Figure 4:
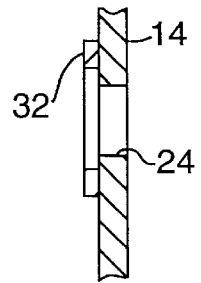

FIG. 3 shows a sealing ring 32 which concentrically surrounds the drop application opening 22 in the cover layer 20 and which is arranged below the cover layer 32, so that it is held in place by the cover layer. The seal ring 20 can, however, also be applied to the outer side of the cover layer 20, as shown in FIG. 4.

FIG. 3 shows a further possibility for the formation of a seal ring, whereby the edge 34 of the measuring opening 24 formed in the carrier layer 14 is so bent outwardly that it in essence forms a seal bead. The seal ring 32 and the seal bead 34 cooperate with surfaces of a measuring device, in which the test card 10 is inserted, to inhibit the applied liquid from escaping outwardly from the area of the drop application opening 22 into the device or into the neighboring test section, or, for example, to seal the measuring optics 26, 28 against stray light.

The test card 10 has regularly spaced recesses 36 along its longitudinal edges into which the transport elements of a measuring device can be received, to mechanically transport the test card 10 in the measuring device. The transport recesses lying between the individual test sections 12 are connected by lines of perforation or other lines of weakening 37, which are provided in all of the superimposed layers 14–20, so that the individual test sections 12 can easily and cleanly be separated from one another. If desired, however, such separation can also be accomplished by a cutting device provided in the associated measuring device.

Figure 5:
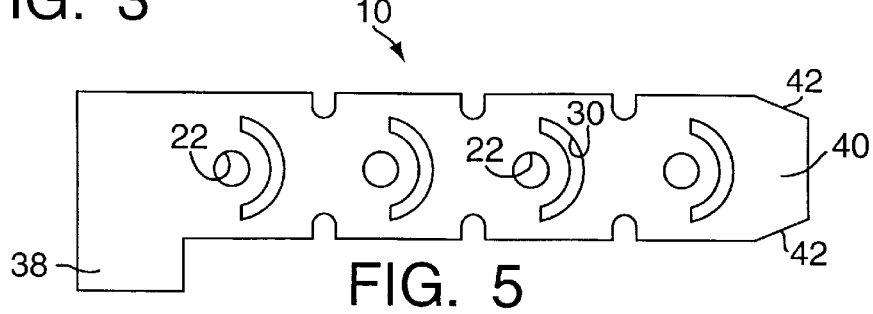

FIG. 5 shows a test card 10 with a widened gripping end 38 and an input end 40, which input end is characterized by inclined surfaces 42 which simplify the insertion of the test card 10 into a measuring device. The widened gripping end 38 simplifies not only the gripping of the test card 10, but also hinders the test card from being incorrectly inserted into the device.

In the case of the embodiment illustrated in FIG. 1, a bar code 44 is printed onto the edge area of the carrier layer 14 which extends outwardly beyond the cover layer 20. This bar code contains information about the test card 10 and the test to be carried out, especially characteristic data for the evaluation of the test reaction. This data can be read by a reading device provided in the measuring device automatically upon the insertion of the test card into the measuring device so that it is assured that the measuring device is supplied with the data required for carrying out the tests with the test card in question. As already mentioned above, this information can also be stored on the test card 10 in various different other ways.

Figure 6:
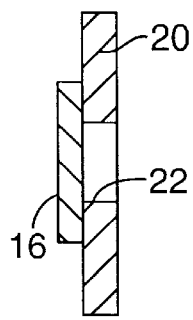

FIG. 6 shows a cross-section through a test card consisting only of a cover layer 20 and a reaction layer 16 connected with the cover layer. In this case, the cover layer 20 can have the transport recesses. Such test card can be used if the reaction layer 16 assures a sufficiently fast and uniform distribution of the liquid to be investigated within the test field.

Figure 7:
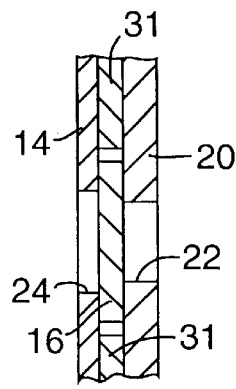

FIG. 7 shows an embodiment in which the distribution layer is likewise omitted, wherein the reaction layer 16 is enclosed between the cover layer 20 and the carrier layer 14, and wherein strips of 31 of a drying media are arranged laterally next to the reaction layer 16. These strips of drying media can also be omitted, in which case the carrier layer 14 and the cover layer 20 engage one another at the edges of the reaction layer 16.

Figure 8:
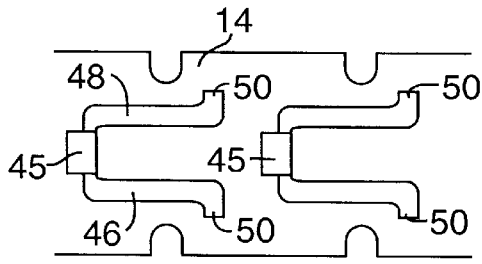

In FIG. 8 a test field 45 consisting of a section of the reaction layer 16 is applied to the carrier layer 14. Further two contact paths 46, 48 are printed onto the carrier layer 14, which contact paths are connected with one another through the test field 45 and at their ends remote from the test field 45 have widened contact pads 50. These contact pads are intended for contact with electrodes of the electrical current measuring device.

Figure 9:
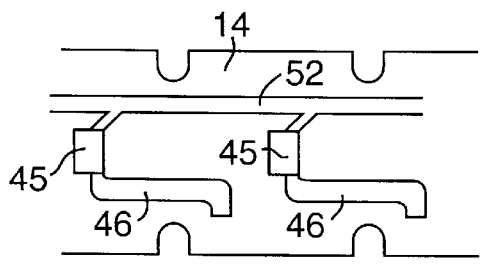

FIG. 9 shows a modified embodiment in which on one side of the test fields 45 a continuous contact path 52 is arranged, whereas on the other sides of the test fields 45, separate contact paths 46, as in the FIG. 8 embodiment, are connected with the test fields 45.

Figure 10:
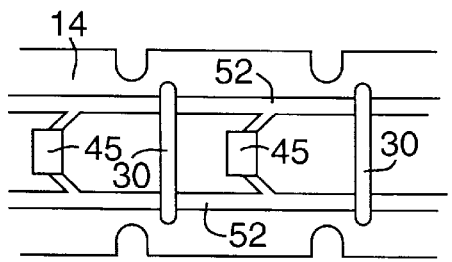

FIG. 10 shows an embodiment in which a continuous contact path 52 is provided on both sides of the test field 45. In this case, the contact paths must be interrupted between the individual test sections 12. This is accomplished in the illustration of FIG. 10 by slots 30 similar to those in the embodiment according to FIGS. 1–5.

Figure 11:
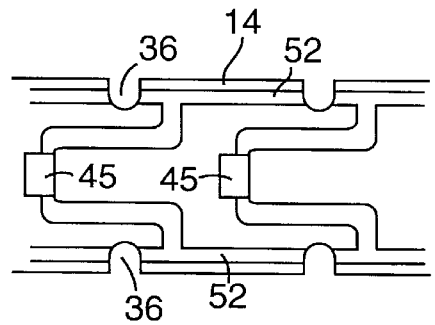

In FIG. 11 the more outwardly lying contact paths 52 are interrupted by the transport recesses 36.

Figure 12:
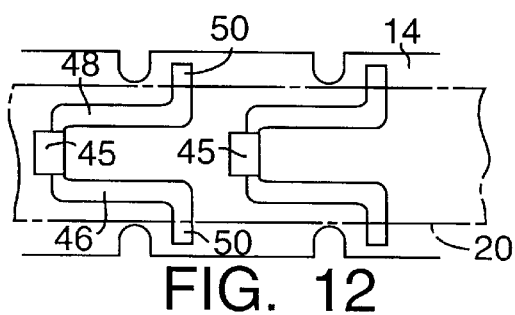

FIG. 12 shows an embodiment similar to FIG. 8, wherein the contact paths 50 project laterally from the cover layer 20, shown in broken line, so that for example by means of a contact spring, the test card position relative to the device can be sensed and can be optically or acoustically indicated. In the case of a motorized drive of the test card in the measuring device, this signal can also be used for shutting off the drive.

Figure 13:
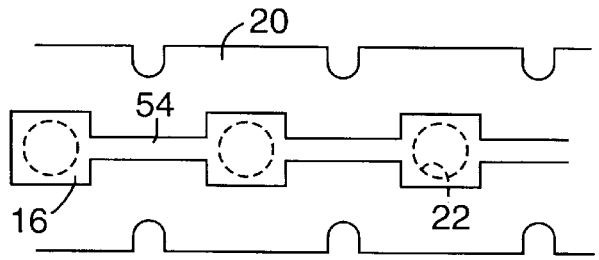

FIG. 13 finally shows an embodiment with a specially shaped reaction layer 16. According to the illustration, this consists of individualizing the test fields, of corresponding wider sections, which individualized test fields are connected with one another by smaller width material bridges 54. This allows the possibility of continuous manufacture from rolls, with at the same time the usage of the relatively expensive reaction layer material being reduced to a minimum.

What is claimed is:

1. A strip-shaped test card for an optical or electrical determination of the concentration of a substance in a liquid, especially a body liquid, with a plurality of identical test sections (12) connected to one another and arranged so as to follow one another in the longitudinal direction of the test card (10), characterized in that the test card (10) has one reaction layer (16) extending along the length of the test card and one cover layer (20) extending along the length of the test card, said reaction layer and cover layer being joined to one another along the length of the test card in overlying relationship and being configured to define the identical test sections, the cover layer having for each of said test sections (12) a drop application opening (22) for the reception of a drop of the liquid to be investigated.

2. A test card according to claim 1, further characterized in that the reaction layer (16) is enclosed between the cover layer (20) and a carrier layer (14), which carrier layer also extends along the length of the test card.

3. A test card according to claim 1, further characterized in that between the reaction layer (16) and the cover layer (12) is arranged a distribution layer (18).

4. A test card according to claim 1, further characterized in that the cover layer (20) is made from an absorbent material.

5. A test card according to claim 1, further characterized in that the cover layer (20) is made from a hydrophobic material.

6. A test card according to claim 2, further characterized in that the carrier layer (14) has a measuring opening (24) for each of said test sections (12).

7. A test card according to claim 6, further characterized in that the measuring opening (24) is one with its longitudinal direction parallel to the longitudinal direction of the test card.

8. A test card according to claim 6, further characterized in that the dimensions of the drop application opening (22) in the cover layer (20) are smaller than the dimensions of the measuring opening (24) in the carrier layer (14).

9. A test card according to claim 2, further characterized in that the carrier layer (14) is made from a transparent material.

10. A test card according to claim 1, further characterized in that the carrier layer (14) and/or the cover layer (20) run in the longitudinal direction of the test card.

11. A test card according to claim 1, further characterized in that the reaction layer (16) and/or the distribution layer (18) are separated between two neighboring test sections (12).

12. A test card according to claim 11, further characterized in that the separation is accomplished by a gap (30) passing through the layers (16, 18).

13. A test card according to claim 12, further characterized in that the gap (30) extends in registration through all layers (14 to 20).

14. A test card according to claim 3, further characterized in that the reaction layer (16) encompasses a larger area than the distribution layer (18).

15. A test card according to claim 1, further characterized in that a drying medium (31) is arranged next to the reaction layer (16).

16. A test card according to claim 1, further characterized in that the cover layer (20) and/or the carrier layer (14) are pre-dried.

17. A test card according to claim 1, further characterized in that it has recesses along its longitudinal edges for cooperation with a test card transport mechanism in a measuring device.

18. A test card according to claim 17, further characterized in that the recesses (36) are each arranged between two neighboring test sections (12).

19. A test card according to claim 1, further characterized in that the layers (14 to 20) have registered lines of weakening between each pair of neighboring test sections (12).

20. A test card according to claim 1, further characterized in that one longitudinal end of the test card (10) is formed as a gripping end (38).

21. A test card according to claim 20, further characterized in that said gripping end (32) is wider than the remainder of the test card (10).

22. A test card according to claim 20, further characterized in that it has inclined insertion guide edges (42) at its end (40) opposite to said gripping end (38).

23. A test card according to claim 1, further characterized in that each test section (12) has a seal ring (32, 34) surrounding the drop application opening (22) and/or the measuring opening (24).

24. A test card according to claim 23, further characterized in that the seal ring (32) is made from a suitable drying medium.

25. A strip-shaped test card for an optical or electrical determination of the concentration of a substance in a liquid, especially a body liquid, with a plurality of test sections (12) connected to one another and arranged so as to follow one another in the longitudinal direction of the test card (10), characterized in that the test card (10) has a reaction layer (16) and a cover layer (20) with the cover layer having for each of said test sections (12) a drop application opening (22) for the reception of a drop of the liquid to be investigated, and in that information is provided on the card identifying the card and/or concerning the carrying out of the tests to be made.

26. A test card according to claim 25, further characterized in that the information is printed in the form of a bar code (44).

27. A test card according to claim 25, further characterized in that a magnetic strip is used as the information carrier.

28. A test card according to claim 25, further characterized in that as the information carrier a hologram is applied to or impressed in the test card.

29. A test card according to claim 25, further characterized in that as an information carrier a resistance layer is provided on the test card.

30. A test card according to claim 25, further characterized in that as an information carrier a memory chip is provided on the test card.

31. A test card according to claim 25, further characterized in that the information is provided in the form of a perforation code in the test card.

32. A test card according to claim 1, further characterized in that two electrical contact paths (46, 48; 52) are provided on the surface of the cover layer (20) facing the reaction layer (16) and/or on the carrier layer (14) within each test section (12), which contact paths are in connection with a section of the reaction layer (16) serving as the test field.

33. A test card according to claim 32, further characterized in that the contact paths (52) run in the longitudinal direction of the card.

34. A test card according to claim 32, further characterized in that both contact paths (52) run in the longitudinal direction of the card and each is interrupted between adjacent test section (12).

35. A test card according to claim 34, further characterized in that the contact paths (52) are interrupted by the transport recesses (36).

36. A test card according to claim 32, further characterized in that the contact paths (46, 48) at least in the area of the associated test fields project laterally from the cover layer (20).

37. A test card according to claim 1, further characterized in that the reaction layer (16) consists of a chain of test fields which are connected with one another by thin bridges.

* * * * *